(12) United States Patent
Chu et al.

(10) Patent No.: US 10,668,189 B2
(45) Date of Patent: Jun. 2, 2020

(54) MEDICAL NEEDLE AND METHOD OF MAINTAINING SHARPNESS OF NEEDLE

(71) Applicant: National Taiwan University of Science and Technology, Taipei (TW)

(72) Inventors: Jinn P. Chu, Taipei (TW); Guei-Huang Jiang, Taipei (TW); Shih-Hsin Chang, Taipei (TW); Ming-Jen Chen, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 231 days.

(21) Appl. No.: 15/874,269

(22) Filed: Jan. 18, 2018

(65) Prior Publication Data

US 2018/0280585 A1    Oct. 4, 2018

(30) Foreign Application Priority Data

Mar. 31, 2017    (TW) .............. 106111302 A

(51) Int. Cl.
| | |
|---|---|
| *B32B 15/00* | (2006.01) |
| *A61L 31/02* | (2006.01) |
| *A61B 17/06* | (2006.01) |
| *A61L 31/04* | (2006.01) |
| *C23C 14/35* | (2006.01) |
| *C23C 14/16* | (2006.01) |
| *A61L 31/08* | (2006.01) |
| *C22C 45/10* | (2006.01) |

(Continued)

(52) U.S. Cl.
CPC ...... *A61L 31/022* (2013.01); *A61B 17/06066* (2013.01); *A61L 31/049* (2013.01); *A61L 31/088* (2013.01); *C22C 45/10* (2013.01); *C23C 14/165* (2013.01); *C23C 14/35* (2013.01); *A61B 2017/0084* (2013.01); *A61B 2017/00526* (2013.01); *A61B 2017/00849* (2013.01); *A61B 2017/00964* (2013.01); *A61M 5/329* (2013.01); *C23C 14/16* (2013.01)

(58) Field of Classification Search
None
See application file for complete search history.

(56) References Cited

U.S. PATENT DOCUMENTS

| | | | |
|---|---|---|---|
| 5,330,441 A * | 7/1994 | Prasad | A61B 17/06066 606/222 |
| 2013/0108888 A1 | 5/2013 | Jang et al. | |
| 2016/0331365 A1 | 11/2016 | Chu et al. | |

OTHER PUBLICATIONS

Chu et al., "Non-stick syringe needles: Beneficial effects of thin film metallic glass coating," Scientific Reports, 6, 31847, 2016, pp. 1-7.

* cited by examiner

*Primary Examiner* — Seth Dumbris
(74) *Attorney, Agent, or Firm* — JCIPRNET

(57) ABSTRACT

Disclosed is a medical needle used for performing a piercing or insertion operation on an object repetitively, the medical needle comprising a needle body and a metallic glass material layer formed on a surface of the needle body, the metallic glass material layer comprising an alloy consisting of aluminum, zirconium, copper and tantalum. With the presence of the metallic glass material layer covering the needle body, the medical needle may maintain its sharpness after having performed multiple piercing or insertion operations to enhance durability, minimize the increase of maximum piercing or insertion force resulted from piercing or insertion operations, and decrease injury to the object caused by piercing or insertion operations.

16 Claims, 7 Drawing Sheets

(51) Int. Cl.
*A61B 17/00* (2006.01)
*A61M 5/32* (2006.01)

MEDICAL NEEDLE AND METHOD OF MAINTAINING SHARPNESS OF NEEDLE

CROSS-REFERENCE TO RELATED APPLICATION

This application claims the priority benefit of Taiwan Patent Application No. 106111302, filed on Mar. 31, 2017. The entirety of the above-mentioned patent application is hereby incorporated by reference herein and made a part of this specification.

BACKGROUND

1. Field of the Invention

The present disclosure relates to a medical needle and more particularly to a medical needle capable of maintaining sharpness after multiple piercing or insertion operations.

2. Description of Related Art

Medical needles are essential for many types of surgery. As an example of medical needles, suture needles are required for sewing tissue wounds formed on skin or organ caused by injury or surgery; to form wound closure, peripheral tissues of the wound are sewn and pierced by suture needles several times to suture the wound with suture thread.

Extra care should be taken when using a suture needle to pierce the tissue so as to avoid injuring other tissues due to improper force applied, and therefore the sharpness and durability of a suture needle is extremely important. In addition, if the same suture needle is used repetitively in the whole sewing process, the suture needle becomes blunter when the number of piercing operation increases, such that the user has to exert more force on the suture needle or change for a new suture needle, which causes inconvenience to the surgery process and increases the costs; for a precision surgery, a small variation in force exerted may significantly change the surgery outcome, so a user will have to replace the suture needle before it becomes blunt after several piercing operations and use a new one to continue the suturing process. As such, medical costs will be increased by high replacement rate.

To overcome the aforesaid problems, some commercially available suture needles are coated with lubricant in order to enhance their durability. While those suture needles may achieve slightly more piercing operations, lubricant will gradually decrease or get dried when the number of piercing increases, so the aforesaid problems cannot be solved effectively.

Therefore, there is a need to provide a medical needle capable of maintaining sharpness after multiple piercing or insertion operations and achieving high durability so as to minimize potential injury to tissues.

SUMMARY

An objective of the present disclosure is to provide a medical needle capable of maintaining sharpness after repetitive piercing or insertion operations.

To achieve the above and other objectives, provided herein is a medical needle comprising a needle body and a metallic glass material layer formed on the surface of the needle body, wherein the metallic glass material layer comprises an alloy consisting of aluminum, zirconium, copper and tantalum, wherein the presence of the metallic glass material layer covering the needle body maintains a sharpness of the medical needle such that an increase percentage of maximum piercing or insertion force of a nth piercing or insertion operation relative to a first piercing or insertion operation, represented by $((X_n-X_1)/X_1)*100\%$, is not greater than 18.9%, given that: N represents the number of piercing or insertion operations performed by the medical needle on an object and ranges from 5 to 80 inclusive; n is a natural number from 5 to N; $X_1$ represents the maximum piercing or insertion force required for the first piercing or insertion operation; and $X_n$ represents the maximum piercing or insertion force required for the nth piercing or insertion operation.

In one embodiment, the needle body is a curved 6/0 cutting needle and the object is a rubber, wherein when N is 40, the value of $((X_{40}-X_1)/X_1)*100\%$ of the medical needle is not greater than 0.337-fold of that of a needle body without the metallic glass material layer having performed 40 piercing or insertion operations.

In one embodiment, the needle body is a curved 7/0 taper needle and the object is a rubber, wherein when N is 40, the value of $((X_{40}-X_1)/X_1)*100\%$ of the medical needle is not greater than 0.143-fold of that of a needle body without the metallic glass material layer having performed 40 piercing or insertion operations.

In one embodiment, the needle body is a curved 6/0 cutting needle and the object is a rubber, wherein when N is 40, the value of $((X_{40}-X_1)/X_1)*100\%$ is not greater than 9.9%.

In one embodiment, the needle body is a curved 7/0 taper needle and the object is a rubber, wherein when N is 40, the value of $((X_{40}-X_1)/X_1)*100\%$ is not greater than 6.1%.

In one embodiment, the needle body is a curved 6/0 cutting needle and the object is an artificial blood vessel made of polymeric material, wherein when N is 40, the value of $((X_{40}-X_1)/X_1)*100\%$ is between −1.5% and 5%.

In one embodiment, the needle body is selected from a cutting needle, a taper needle, a straight needle and a curved needle.

In one embodiment, the metallic glass material layer has an amorphous structure which renders a broad diffraction peak only in a low angle area of between 30° and 40° as measured by X-ray diffraction.

In one embodiment, the metallic glass material layer comprises $Zr_{52.5-53.5}Cu_{32.5-33.5}Al_{8.5-9.5}Ta_{4.5-5.5}$, such as $Zr_{53}Cu_{33}Al_9Ta_5$.

In one embodiment, the metallic glass material layer has a hardness of 700 to 2000 HV.

In one embodiment, the metallic glass material layer is formed by a magnetron sputtering process in which the needle body and a target are placed in a vacuum environment with a work pressure of 0.5 to 4 mTorr, a distance between the needle body and the target is set at 8 to 12 cm, a radio frequency energy is provided between the needle body and the target, and the power density of the target is 3.65 to 10.96 W/cm².

In one embodiment, the metallic glass material layer formed by the aforesaid magnetron sputtering process has a surface roughness of between 0.44 and 0.54 nm.

Also provided herein is a medical needle comprising a needle body and a metallic glass material layer formed on the surface of the needle body, wherein the metallic glass material layer comprises an alloy consisting of aluminum, zirconium, copper and tantalum, wherein, given that the medical needle is subject to N times of piercing or insertion operation, wherein N ranges from 5 to 80 inclusive, and given that a maximum piercing or insertion force of a nth piercing or insertion operation is $X_n$, wherein n is a natural number from 1 to N, a dataset of every n and $X_n$ in the N times of piercing or insertion operation is characterized by having a slope of simple linear regression estimated using the ordinary least squares method of not greater than 0.00654 as calculated according to the formula below:

$$a' = \sum_{n=1}^{N} (X_n - \overline{X_N})(n - \overline{N}) / \sum_{n=1}^{N} (X_n - \overline{X_N})^2$$

wherein a' represents the slope, $\overline{X_N}$ represents an average maximum piercing or insertion force during the N times of piercing or insertion operation, and $\overline{N}$ represents an average of 1 to N.

In one embodiment, the slope is a negative value.

In one embodiment, the needle body is a curved 6/0 cutting needle and the object is a rubber, wherein when N is 40, the slope is between 0.00131 and 0.00654.

In one embodiment, the needle body is a curved 7/0 taper needle and the object is a rubber, wherein when N is 40, the slope is between 0.00023 and 0.00133.

In one embodiment, the needle body is a curved 6/0 cutting needle and the object is an artificial blood vessel made of polymeric material, wherein when N is 40, the slope is between −0.00020 and −0.00047.

Also provided herein is a method of maintaining sharpness of a needle, comprising: providing a needle body; on a surface of the needle body, forming a metallic glass material layer comprising an alloy consisting of aluminum, zirconium, copper and tantalum; and using the needle body to perform N times of piercing or insertion operation on an object, wherein the depth of each piercing or insertion operation ranges from 1 to 10 mm, the speed of each piercing or insertion operation ranges from 10 to 100 mm/min, and N ranges from 5 to 80 inclusive; wherein an increase percentage of maximum piercing or insertion force of a nth piercing or insertion operation relative to a first piercing or insertion operation is not greater than 18.9% given that n is a natural number from 5 to N.

In one embodiment, the medical needle comprises a needle body and a metallic glass material layer formed on the surface of the needle body, wherein the metallic glass material layer comprises an alloy consisting of aluminum, zirconium, copper and tantalum. With the presence of the metallic glass material layer covering the needle body, the medical needle may maintain its sharpness after having performed a first number of piercing or insertion operations, minimize the increase of maximum piercing or insertion force resulted from piercing or insertion operations to enhance durability, and decrease injury to the object caused by piercing or insertion operation, wherein the first number is less than 10.

In one embodiment, the increase percentage of maximum piercing or insertion force of a medical needle with the metallic glass material layer after having performed a first number of piercing or insertion operations is less than that of a medical needle without the metallic glass material layer after having performed the first number of piercing or insertion operations.

In one embodiment, if the first number is 40, the increase percentage of maximum piercing or insertion force of a medical needle without the metallic glass material layer after having performed the first number of piercing or insertion operations is at least 2.4-fold of the increase percentage of maximum piercing or insertion force of a medical needle with the metallic glass material layer after having performed the first number of piercing or insertion operations.

In one embodiment, if the first number is 40, the increase percentage of maximum piercing or insertion force of a medical needle according to the present disclosure after having performed the first number of piercing or insertion operations relative to the first piercing or insertion operation is less than 10%.

In one embodiment, if the first number is 40, the increase percentage of maximum piercing or insertion force of a medical needle according to the present disclosure after having performed the first number of piercing or insertion operations relative to the first piercing or insertion operation is between 4% and 10%.

In one embodiment, the slope of linear regression of a dataset of maximum piercing or insertion force of each piercing or insertion operation within the first number of times is less than 0.007.

DETAILED DESCRIPTION OF EMBODIMENTS

Since various aspects and embodiments are merely exemplary and not limiting, after reading this specification, skilled artisans appreciate that other aspects and embodiments are possible without departing from the scope of the disclosure. Other features and benefits of any one or more of the embodiments will be apparent from the following detailed description and the claims.

As used herein, the terms "comprises," "comprising," "includes," "including," "has," "having" and any other variation thereof are intended to cover a non-exclusive inclusion. For example, a component or structure that comprises a list of elements is not necessarily limited to only those elements but may include other elements not expressly listed or inherent to such component or structure.

The medical needle disclosed herein is used for performing a piercing or insertion operation on an object repetitively, wherein the object may be a human being or organism, which is simulated by rubber or other organic material in the experiments below. As used herein, a piercing or insertion operation may include insertion operation or piercing operation, wherein insertion operation refers to using a needle to perform insertion and retraction on an object, and piercing operation refers to piercing through an object with a needle from one side to the other.

Figure 1:
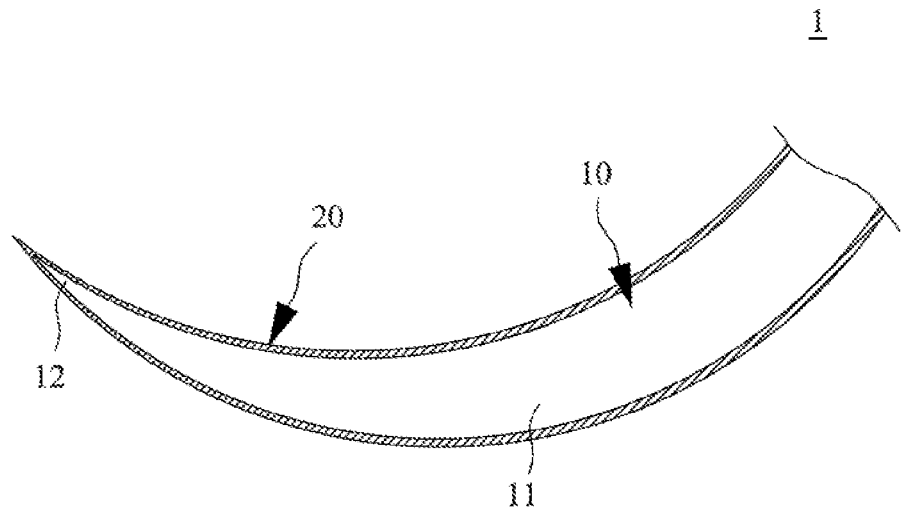
FIG. 1 illustrates a partial cross-sectional view of a first embodiment of the medical needle.
Figure 2:
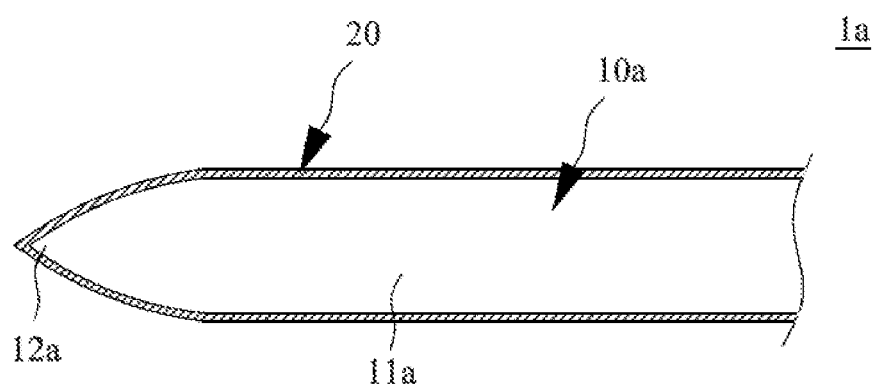
FIG. 2 illustrates a partial cross-sectional view of a second embodiment of the medical needle.

Refer to FIG. 1 and FIG. 2. As shown, a medical needle 1 or 1a comprises a needle body 10 or 10a and a metallic glass material layer 20. The needle body 10 or 10a is a solid needle such as a suture needle or other needle for surgery, but the needle body may also have a hollowed portion or a hollow structure. Depending on different needs and structural designs, the needle body 10 or 10a may be configured as a curved needle, a straight needle, a cutting needle, a taper needle or a combination thereof. The needle body 10 or 10a comprises a body 11 or 11a and a needle point 12 or 12a, wherein the curved needle refers to a needle body 10 with a curved body 11 and the straight needle refers to a needle body 10a with a straight body 11a; the body 11 or 11a may have a triangular, prismatic or round cross section; the cutting needle refers to a needle body 10 or 10a with a body 11 or 11a having a triangular or prismatic cross section and the taper needle refers to a needle body 10 or 10a with a body 11 or 11a having a round cross section; in addition, the needle point 12 or 12a may be configured as a round point, a triangular point or a spade point. In one example, as illustrated in FIG. 1, the needle body 10 is configured as a curved suture needle, but a different configuration may also be used. In another example, the needle body 10 is configured as the straight needle 10a as illustrated in FIG. 2. The needle body 10 may be made of at least a metal or an alloy, such as made of Ti, Al, Cu, Fe, or an alloy thereof.

The metallic glass material layer 20 is formed on the surface of the needle body 10 to form a thin film coating covering the body 11 and the needle point 12 of the needle body 10. In one embodiment, the metallic glass material layer 20 may be made by, but not limited to, subjecting the needle body 10 to a magnetron sputtering process. The metallic glass material layer 20 may comprise an alloy consisting of aluminum, zirconium, copper and tantalum (Al—Zr—Cu—Ta). In one embodiment, the metallic glass material layer 20 comprises $Zr_{53}Cu_{33}Al_9Ta_5$. During the magnetron sputtering, the alloy for forming the metallic glass material layer 20 serves as a cathode target, which is subject to an electric field and a circular closed magnetic field, such that secondary electrons generated by sputtering and leaving from the target will change the direction of motion under the influence of electric field and magnetic field to collide with gas atoms, facilitating the ionization of gas and rapid deposition of the target material on the needle body 10 connected with the anode. In one embodiment, the magnetron sputtering may be driven by direct current or radio frequency with the power controlled at 100 to 300 W and work pressure of 4 mTorr, but other conditions may also be used.

The metallic glass material layer 20 has an amorphous structure, which means that there is no regular arrangement of atoms, such that the metallic glass material layer 20 is free from defects associated with the crystalline state such as grain boundaries, dislocations and stacking faults; in addition, the metallic glass material layer 20 has a hardness of 700 to 2000 Vickers pyramid number (HV), providing excellent yield strength, hardness, elastic deformation limit, corrosion resistance, wear resistance and fatigue resistance.

The amorphous structure may be characterized by different methods, such as X-ray diffraction (XRD) and differential scanning calorimeter (DSC) analysis. X-ray diffraction analysis involves scanning the material with X-ray diffraction to produce an X-ray diffraction pattern useful for the determination of an amorphous structure. For crystalline metals or alloys, the presence of periodic atom arrangement renders multiple diffraction peaks in the X-ray diffraction pattern; however, for the metallic glass material layer 20 comprising an alloy with an amorphous structure, there is only one broad diffraction peak in the X-ray diffraction pattern within the low angle area between 30° and 40°.

Differential scanning calorimeter analysis involves characterization of material from its thermal property. For crystalline metals or alloys, melting point is the only transition between solid state and liquid state; however, for the metallic glass material layer 20 comprising an alloy with an amorphous structure, unique amorphous thermal property parameters exist during the transition from the solid state to the liquid state, such as the glass transition temperature (Tg) and the crystalline temperature (Tx), which may be obtained by the differential scanning calorimeter analysis.

Specifically, the medical needles 1 disclosed herein may be prepared using a unique set of conditions different from conventional magnetron sputtering processes. During a conventional magnetron sputtering process, a needle body and a metallic glass alloy target are placed in a vacuum environment with a work pressure of 5 to 10 mTorr, a distance between the needle body and the target is set at 15 to 20 cm, direct current (DC) is supplied between the needle body and the target, and the target power density is about 15.8 W/cm², using the conditions to perform magnetron sputtering of the metallic glass material layer on the needle body. In contrast, the present disclosure uses a magnetron sputtering process wherein the needle body and the metallic glass alloy target are placed in a vacuum environment with a work pressure of 0.5 to 4 mTorr (preferably 1 to 3 mTorr and more preferably 1 mTorr), a distance between the needle body and the target is set at 8 to 12 cm (preferably 10 cm), particularly a radio frequency (RF) is provided between the needle body and the target, and the target power density is about 3.65 to 10.96 W/cm² (preferably 4 W/cm²). The aforesaid conditions were used to perform magnetron sputtering of the metallic glass material on the needle body of the present disclosure.

Refer to Table 1, which illustrates the values associated with several physical properties measured from metallic glass material layers of experimental group and comparative group, wherein the experimental group represents the medical needle prepared by using the magnetron sputtering conditions according to the present disclosure, and the comparative group represents the medical needle prepared by using the conventional magnetron sputtering. Electron microscope observations of cross-sectional structure and surface structure images of the metallic glass material layers indicate the presence of column structures found from the cross-sectional structure of the metallic glass material layer in the comparative group. Due to the weaker bonding between the column structures, the metallic glass material layer of the comparative group has a hardness of about 3.9 Gpa and a Young's modulus of about 56.7 Gpa; on the other hand, the metallic glass material layer of the experimental group has a homogeneous structure and a smoother surface. Particularly, the metallic glass material layer of the experimental group has a hardness of about 10.4 Gpa and a Young's modulus of about 151 Gpa, which are significantly higher than those of the comparative group.

Moreover, the surface roughness (i.e., root mean square roughness) of respective metallic glass material layers was measured by an atomic force microscope. The results show that the metallic glass material layer of the comparative group has a surface roughness of about 1.74 to 2.24 nm, and the metallic glass material layer of the experimental group has a surface roughness of about 0.44 to 0.54 nm, preferably 0.49 nm, indicating that the comparative group has a higher surface roughness, such as 3.22 to 5.09 times higher or preferably 3.55 to 4.57 times higher than the experimental group; in addition, the coefficient of friction of the comparative group is higher, too. Accordingly, these results prove that the medical needles prepared by using a magnetron sputtering process with preferred conditions described above may have a metallic glass material layer with lower surface roughness and lower coefficient of friction and a smoother needle surface than those prepared with conventional magnetron sputtering conditions, making the medical needles according to the present disclosure more suitable for piercing or insertion operation.

TABLE 1

|  | Hardness | Young's modulus | Coefficient of friction | Surface roughness (Rq) |
|---|---|---|---|---|
| Comparative group | 3.9 GPa | 56.7 GPa | 0.085 | 1.74 to 2.24 nm |
| Experimental group | 10.4 GPa | 151 GPa | 0.046 | 0.44 to 0.54 nm |

Medical needles 1 disclosed herein are used as the experimental group for comparison with needles with different conditions as the comparative group in the piercing or insertion experiments to further investigate the effects and features of the medical needles 1 of the present disclosure. Since most commercial needles are pre-coated with a lubricant layer, in the following experiments, commercial needles are unpacked, cleaned to remove the lubricant layer and then coated with the metallic glass material layer 20 to serve as the experimental group A1-A5; on the other hand, commercial needles unpacked and cleaned to remove the lubricant layer (e.g., needles without any surface coating, also known as naked needles) serve as the comparative group B1-B5, and needles unpacked but without removing the lubricant layer serve as the comparative group C1-C5 in the piercing or insertion experiments. The piercing or insertion experiments are carried out under atmospheric pressure; a material tester of model number MTS Criterion 42.503 Test System is used to hold the specimens from the experimental group and comparative group to perform piercing or insertion operation at a specified speed (e.g., 10 mm/min to 100 mm/min) on an object (e.g., polyurethane rubber with a Shore hardness of 50) by a specified depth (e.g., 1 mm to 10 mm), and data are recorded after a first number of piercing or insertion operations. In various embodiments, the first number may be not less than 5, such as 10 to 80 times, for example 10, 20, 30, 40, 50, 60, 70, or 80 times, but not limited thereto. Suitable needles comprise, but not limited to, 6/0 cutting needles, 7/0 taper needles, 18 G straight needles and 21 G straight needles, and needles of different specifications may also be used.

In one embodiment, each medical needle 1 is subject to N times of piercing or insertion operation, wherein N ranges from 5 to 80 inclusive. $X_1$ represents the maximum piercing or insertion force required for the first piercing or insertion operation of the medical needle 1, and $X_n$ represents the maximum piercing or insertion force required for the nth piercing or insertion operation of the medical needle 1, such that an increase percentage of the maximum piercing or insertion force of the nth piercing or insertion operation relative to the first piercing or insertion operation may be represented by $((X_n-X_1)/X_1)*100\%$, wherein n is a natural number from 5 to N.

In this embodiment, curved 6/0 cutting needles (curved needles with curvature of ⅜ circle, chord length of 12 mm, and body diameter of about 4 mm) and an object made of rubber are used. Each of the experimental group A1-A5, comparative group B1-B5 and comparative group C1-C5 contains five 6/0 cutting needle specimens; the speed and depth of piercing or insertion operation is set at 30 mm/min and 3.5 mm respectively to carry out 40 piercing or insertion operations, and the maximum piercing or insertion force after every 10 piercing or insertion operations is recorded to calculate the percentage of increased maximum piercing or insertion force after every 10 piercing or insertion operations, as listed in Table 2. As used herein, the maximum piercing or insertion force refers to the maximum force (unit: N) applied to the needle in order to reach the specified piercing or insertion depth (e.g., 3.5 mm) in each piercing or insertion operation. The increase percentage of maximum piercing or insertion force refers to the percentage (unit: %) of force increased of a piercing or insertion operation relative to the first piercing or insertion operation.

TABLE 2

|  | 1 time | 10 times | increase percentage | 20 times | increase percentage | 30 times | increase percentage | 40 times | increase percentage | slope |
|---|---|---|---|---|---|---|---|---|---|---|
| A1 | 1.53 | 1.55 | 1.3% | 1.51 | −1.3% | 1.61 | 5.2% | 1.64 | 7.1% | 0.00131 |
| A2 | 1.59 | 1.66 | 4.4% | 1.89 | 18.9% | 1.80 | 13.2% | 1.73 | 8.8% | 0.00654 |
| A3 | 1.45 | 1.44 | −0.7% | 1.53 | 5.5% | 1.51 | 4.1% | 1.59 | 9.9% | 0.00536 |
| A4 | 2.15 | 1.99 | −7.4% | 2.06 | −4.2% | 2.17 | 0.9% | 2.27 | 5.6% | 0.00157 |
| A5 | 2.01 | 1.94 | −3.5% | 2.21 | 10.0% | 2.08 | 3.5% | 2.11 | 4.9% | 0.00199 |
| B1 | 1.70 | 2.41 | 41.8% | 2.49 | 46.5% | 2.65 | 55.9% | 2.40 | 41.2% | 0.01652 |
| B2 | 1.40 | 1.69 | 20.7% | 1.84 | 31.4% | 1.71 | 22.1% | 1.91 | 36.4% | 0.00860 |
| B3 | 1.30 | 1.66 | 27.7% | 1.71 | 31.5% | 1.82 | 40.0% | 1.87 | 43.8% | 0.00860 |
| B4 | 1.80 | 1.97 | 9.4% | 2.22 | 23.3% | 2.25 | 25.0% | 2.33 | 29.4% | 0.01136 |
| B5 | 1.50 | 1.89 | 26.0% | 2.10 | 40.0% | 2.23 | 48.7% | 2.17 | 44.7% | 0.01554 |
| C1 | 1.50 | 1.93 | 28.7% | 2.10 | 40.0% | 2.17 | 44.7% | 2.19 | 46.0% | 0.01271 |
| C2 | 1.33 | 1.80 | 35.3% | 1.96 | 47.4% | 1.98 | 48.9% | 2.00 | 50.4% | 0.01192 |
| C3 | 1.51 | 2.03 | 34.4% | 2.25 | 49.0% | 2.26 | 49.7% | 2.28 | 50.9% | 0.01500 |
| C4 | 1.48 | 1.88 | 27.0% | 2.13 | 43.9% | 2.20 | 48.6% | 2.16 | 45.9% | 0.01476 |
| C5 | 1.48 | 2.07 | 39.9% | 2.26 | 52.7% | 2.35 | 58.8% | 2.43 | 64.2% | 0.01758 |

As shown in Table 2, the increase percentage of maximum piercing or insertion force after every 10 piercing or insertion operations of the experimental group A1-A5, i.e., 6/0 cutting needles coated with the metallic glass material layer 20, is less than that of the comparative group B1-B5 and comparative group C1-C5; moreover, some experimental data even indicate reduced maximum piercing or insertion force after operations, i.e., negative increase percentage. In other words, according to the results in Table 2, the increase percentage of maximum piercing or insertion force of a medical needle with the metallic glass material layer after having performed a certain number (e.g., no less than 10, such as 10 to 80 times) of piercing or insertion operations is significantly less than that of a medical needle without the metallic glass material layer after having performed the same number of piercing or insertion operations. From the results of the experimental group A1-A5 in Table 2, with the presence of the metallic glass material layer 20 covering the surface of the 6/0 cutting needles, the greatest increase percentage in the experimental group A1-A5 after every 10 piercing or insertion operations relative to the first piercing or insertion operation is 18.9%, which lies in the experimental group A2 after 20 piercing or insertion operations; that is, in this embodiment, for all specimens of the experimental group A1-A5, the increase percentage of maximum piercing or insertion force of a nth piercing or insertion operation relative to the first piercing or insertion operation, represented by $((X_n-X_1)/X_1)*100\%$, is not greater than 18.9%.

Similarly, from the results of the experimental group A1-A5 in Table 2, when the needle body is a curved 6/0 cutting needle, the object is rubber, and the number of piercing or insertion operations N is 40, the greatest increase percentage in the experimental group A1-A5 after 40 piercing or insertion operations relative to the first piercing or insertion operation, represented by $((X_{40}-X_1)/X_1)*100\%$, is 9.9%, which lies in the experimental group A3; that is, in this embodiment, for all specimens of the experimental group A1-A5, the increase percentage of maximum piercing or insertion force of the 40th piercing or insertion operation relative to the first piercing or insertion operation, i.e., $((X_n-X_1)/X_1)*100\%$, is not greater than 9.9%. Under the same conditions, as shown in Table 2, for the comparative groups B1-B5 and C1-C5 in which the needle body of the 6/0 cutting needle is not coated with the metallic glass material layer, when the number of piercing or insertion operations N is 40, the minimum increase percentage of maximum piercing or insertion force after 40 piercing or insertion operations relative to the first piercing or insertion operation is 29.4%, which lies in the comparative group B4. Accordingly, when the needle body is a curved 6/0 cutting needle, the object is rubber, and the number of piercing or insertion operations N is 40, the greatest increase percentage of maximum piercing or insertion force after 40 piercing or insertion operations relative to the first piercing or insertion operation, represented by $((X_{40}-X_1)/X_1)*100\%$, of the experimental group A3 (9.9%), is not greater than 0.337-fold of the minimum increase percentage of maximum piercing or insertion force after 40 piercing or insertion operations relative to the first piercing or insertion operation of the comparative group B4 (29.4%). In one embodiment, compared with a needle without the metallic glass material layer, the medical needle according to the present disclosure, after 10 piercing or insertion operations, has an increase percentage of the maximum piercing or insertion force of less than or equal to 10%, such as between −10% and 10%, preferably between −10% and 5%; after 20 piercing or insertion operations, an increase percentage of the maximum piercing or insertion force is less than or equal to 20%, such as between −10% and 20%, preferably between −5% and 10%; after 30 piercing or insertion operations, an increase percentage of the maximum piercing or insertion force is less than or equal to 20%, such as between 0% and 15%, preferably between 0% and 10%; after 40 piercing or insertion operations, an increase percentage of the maximum piercing or insertion force is less than or equal to 20%, such as between 0% and 20%, preferably between 0% and 10%.

In addition, 6/0 cutting needles coated with the metallic glass material layer 20 in the experimental group A1-A5 show significantly inhibited increase percentage of the maximum piercing or insertion force as compared with the comparative groups B1-B5 and C1-C5. From the results in Table 2, for the specimens in the comparative group B1-B5 without the metallic glass material layer, after 40 piercing or insertion operations, the increase percentage of the maximum piercing or insertion force, even if the minimal one (29.4%) is chosen from different batches, is at least 2.9-fold of the greatest increase percentage (9.9%) of the maximum piercing or insertion force of the specimens in the experimental group A1-A5 after 40 piercing or insertion operations, such as between 2-fold and 3-fold; similarly, for the specimens in the comparative group C1-C5, after 40 piercing or insertion operations, the increase percentage of the maximum piercing or insertion force, even if the minimal one (45.9%) is chosen, is at least 4.6-fold of the greatest increase percentage (9.9%) of the maximum piercing or insertion force of the specimens in the experimental group A1-A5 after 40 piercing or insertion operations, such as between 4-fold and 5-fold. Accordingly, the data above are sufficient to prove that the medical needle 1 disclosed herein may inhibit the increase of maximum piercing or insertion force much better than needles only coated with a lubricant layer and naked needles without a lubricant layer.

Moreover, according to the results in Table 2, for the experimental group A1-A5, the specimens subject to 40 piercing or insertion operations shows less than 10%, preferably between 4% and 10%, in the increase percentage of the maximum piercing or insertion force relative to those subject to 1 piercing or insertion operation. Therefore, with the presence of the metallic glass material layer 20 covering the needle body 10, the medical needle 1 of the present disclosure may maintain its sharpness after having performed multiple piercing or insertion operations, minimize the increase of maximum piercing or insertion force resulted from piercing or insertion operations to enhance durability, and decrease injury to the object caused by piercing or insertion operation, thereby effectively inhibiting the increase percentage of the maximum piercing or insertion force after multiple piercing or insertion operations and providing long-term protection to the needle body 10.

Figure 3:
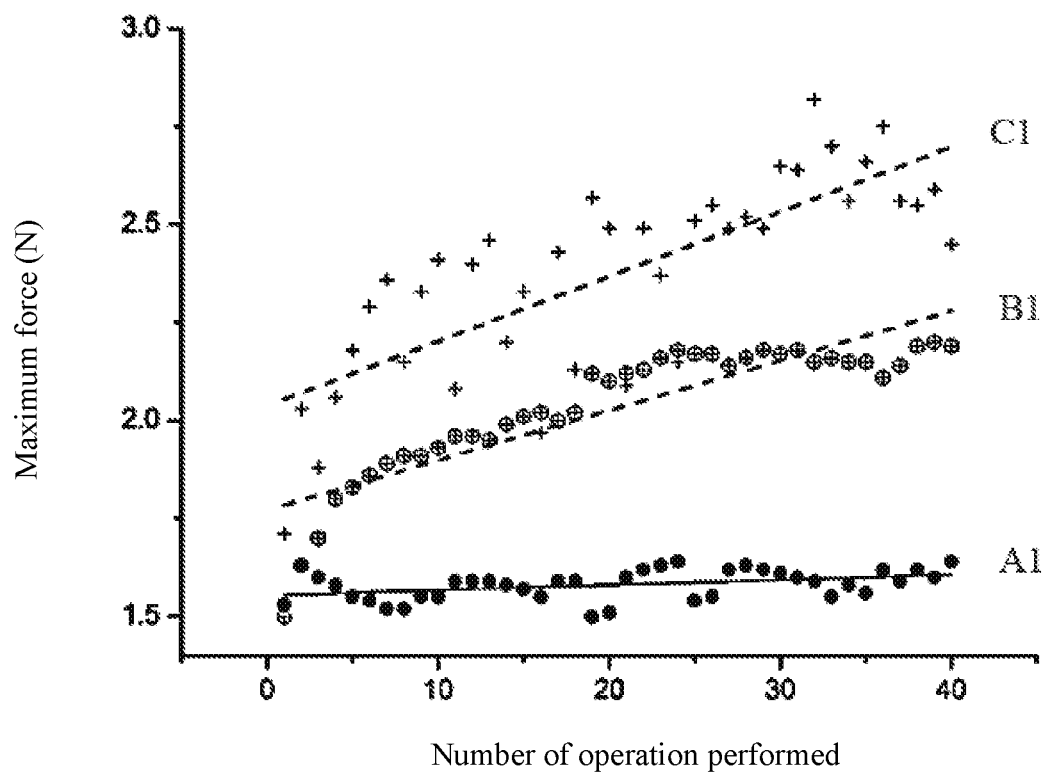
FIG. 3 illustrates a scatter plot of maximum piercing or insertion force of each of 40 piercing or insertion operations of the experimental group A1, comparative group B1 and comparative group C1 listed in Table 2.

Refer to FIG. 3. FIG. 3 illustrates a scatter plot of maximum piercing or insertion force of each of 40 piercing or insertion operations of the experimental group A1, comparative group B1 and comparative group C1, wherein the horizontal axis represents the number of piercing or insertion operation and the vertical axis represents the maximum piercing or insertion force corresponding to each operation. A simple linear regression may be made for each of the experimental group A1, comparative group B1 and comparative group C1 to obtain a trend line representing the ascending trend of the maximum piercing or insertion force relative to the number of piercing or insertion operation, wherein each trend line has a slope.

Each medical needle 1 is subject to N times of piercing or insertion operation, wherein N ranges from 5 to 80 inclusive. Given that a maximum piercing or insertion force of a nth piercing or insertion operation is $X_n$, wherein n is a natural number from 1 to N, a dataset of every n and $X_n$ in the N times of piercing or insertion operation is characterized by having a slope of simple linear regression estimated using the ordinary least squares method as calculated according to the formula below:

$$a' = \sum_{n=1}^{N} (X_n - \overline{X_N})(n - \overline{N}) / \sum_{n=1}^{N} (X_n - \overline{X_N})^2$$

wherein a' represents the slope, $\overline{X_N}$ represents an average maximum piercing or insertion force during the N times of piercing or insertion operation, and $\overline{N}$ represents an average of 1 to N.

As shown in FIG. 3, for the 6/0 cutting needle coated with the metallic glass material layer 20 in the experimental group A1, the trend line has a gentle slope than those of the comparative groups B1 and C1, indicating that the medical needle of the present disclosure can effectively inhibit the increase of maximum piercing or insertion force caused by piercing operations. The slope of the trend line of the experimental group A1 is about 0.00131, significantly less than that of the comparative group B1 (0.01652) and that of the comparative group C1 (0.01271).

In one embodiment, based on the scatter plot of 40 piercing or insertion operations (horizontal axis) and the corresponding maximum piercing or insertion forces (vertical axis), the tread line obtained has a slope of less than 0.017, preferably less than 0.012, such as between 0.001 and 0.012, preferably between 0.001 and 0.007.

Furthermore, a simple linear regression may be made for each of the experimental group A1-A5, comparative group B1-B5 and comparative group C1-C5 to obtain a trend line and its slope representing the ascending trend of the maximum piercing or insertion force relative to the number of piercing or insertion operation. As shown in Table 2, the experimental group A1-A5, the comparative group B1-B5 and the comparative group C1-C5 all have a trend line with a positive slope; when the needle body is a curved 6/0 cutting needle, the object is rubber, and the piercing or insertion operation number N is 40, a dataset of every n and $X_n$ of the piercing or insertion operations is characterized by having a slope of simple linear regression estimated using the ordinary least squares method, wherein the slope a' of each trend line of the experimental group A1-A5 is between 0.00131 and 0.00654, and the maximum slope 0.00654 lies in the experimental group A2; in other words, in this embodiment, the slope of the trend line of any one in the experimental group A1-A5 is not greater than 0.00654. As shown in Table 2, for the comparative group B1-B5 and the comparative group C1-C5 which represent 6/0 cutting needles without the metallic glass material layer, under the same condition, when the piercing or insertion operation number N is 40, a dataset of every n and $X_n$ of the piercing or insertion operations is also characterized by having a slope of simple linear regression estimated using the ordinary least squares method, wherein the slope a' of each trend line of the comparative group B1-B5 is between 0.00860 and 0.01652, and the slope a' of each trend line of the comparative group C1-C5 is between 0.01192 and 0.01758. According to the linear regression analysis above, the increase in maximum piercing or insertion force of the experimental group A1-A5 is significantly lower compared with the comparative groups B1-B5 and C1-C5, indicating that after multiple piercing or insertion operations, the metallic glass material layer 20 may serve as a solid lubricant layer of the medical needle to protect the needle body, thereby inhibiting the increase of piercing force required and enhancing the efficacy and durability.

In the following experiments, commercial needles are unpacked, cleaned to remove the lubricant layer and then coated with the metallic glass material layer 20 to serve as the experimental group A6-A10; on the other hand, commercial needles unpacked and cleaned to remove the lubricant layer (naked needles) serve as the comparative group B6-B10, and needles simply unpacked serve as the comparative group C6-C10 in the piercing or insertion experiments. In this embodiment, curved 7/0 taper needles (curved needles with curvature of ⅜ circle, chord length of 10 mm, and body diameter of about 2 mm) and an object made of rubber are used. Each 7/0 taper needle of the experimental group A6-A10, comparative group B6-B10 and comparative group C6-C10 is tested with the speed and depth of piercing or insertion operation set at 30 mm/min and 2.5 mm respectively to carry out 40 piercing or insertion operations, and the maximum piercing or insertion force after every 10 piercing or insertion operations is recorded to calculate the percentage of increased maximum piercing or insertion force after every 10 piercing or insertion operations, as listed in Table 3.

TABLE 3

|     | 1 time | 10 times | increase percentage | 20 times | increase percentage | 30 times | increase percentage | 40 times | increase percentage | slope |
| --- | --- | --- | --- | --- | --- | --- | --- | --- | --- | --- |
| A6  | 0.86 | 0.86 | 0.0%  | 0.89 | 3.5%  | 0.89 | 3.5%  | 0.89 | 3.5%  | 0.00133 |
| A7  | 0.82 | 0.88 | 7.3%  | 0.90 | 9.8%  | 0.89 | 8.5%  | 0.87 | 6.1%  | 0.00086 |
| A8  | 0.94 | 0.99 | 5.3%  | 0.97 | 3.2%  | 1.00 | 6.4%  | 0.96 | 2.1%  | 0.00039 |
| A9  | 0.91 | 0.91 | 0.0%  | 0.93 | 2.2%  | 0.90 | −1.1% | 0.93 | 2.2%  | 0.00023 |
| A10 | 0.84 | 0.86 | 2.4%  | 0.86 | 2.4%  | 0.83 | −1.2% | 0.87 | 3.6%  | 0.00033 |
| B6  | 0.77 | 0.96 | 24.7% | 1.03 | 33.8% | 1.08 | 40.3% | 1.10 | 42.9% | 0.00776 |
| B7  | 0.72 | 0.96 | 33.3% | 1.03 | 43.1% | 1.06 | 47.2% | 1.11 | 54.2% | 0.00738 |
| B8  | 0.75 | 0.92 | 22.7% | 0.98 | 30.7% | 1.03 | 37.3% | 1.08 | 44.0% | 0.00677 |
| B9  | 0.64 | 0.82 | 28.1% | 0.92 | 43.8% | 0.98 | 53.1% | 1.02 | 59.4% | 0.00821 |
| B10 | 0.76 | 0.94 | 23.7% | 1.02 | 34.2% | 1.11 | 46.1% | 1.18 | 55.3% | 0.00909 |
| C6  | 0.69 | 0.92 | 33.3% | 1.05 | 52.2% | 1.03 | 49.3% | 1.14 | 65.2% | 0.00938 |
| C7  | 0.59 | 0.75 | 27.1% | 0.76 | 28.8% | 0.93 | 57.6% | 0.98 | 66.1% | 0.00964 |
| C8  | 0.59 | 0.71 | 20.3% | 0.83 | 40.7% | 0.91 | 54.2% | 0.97 | 64.4% | 0.00956 |
| C9  | 0.62 | 0.86 | 38.7% | 0.96 | 54.8% | 1.00 | 61.3% | 0.93 | 50.0% | 0.00771 |
| C10 | 0.79 | 0.94 | 19.0% | 1.03 | 30.4% | 1.14 | 44.3% | 1.19 | 50.6% | 0.01028 |

As shown in Table 3, the increase percentage of maximum piercing or insertion force after every 10 piercing or insertion operations of the experimental group A6-A10, i.e., 7/0 taper needles coated with the metallic glass material layer 20, is less than that of the comparative group B6-B10 and comparative group C6-C10. In other words, according to the results in Table 3, the increase percentage of maximum piercing or insertion force of a medical needle, even using different types of structural design, with the metallic glass material layer after having performed a certain number (e.g., no less than 10) of piercing or insertion operations is significantly less than that of a medical needle without the metallic glass material layer after having performed the same number of piercing or insertion operations. From the results of the experimental group A6-A10 in Table 3, with the presence of the metallic glass material layer 20 covering the surface of the 7/0 taper needles, the greatest increase percentage in the experimental group A6-A10 after every 10 piercing or insertion operations relative to the first piercing or insertion operation is 9.8%, which lies in the experimental group A7 after 20 piercing or insertion operations; that is, in this embodiment, for all specimens of the experimental group A6-A10, the increase percentage of maximum piercing or insertion force of a nth piercing or insertion operation relative to the first piercing or insertion operation, represented by $((X_n-X_1)/X_1)*100\%$, is not greater than 18.9%, too. Similarly, from the results of the experimental group A6-A10 in Table 3, when the needle body is a curved 7/0 taper needle, the object is rubber, and the number of piercing or insertion operations N is 40, the greatest increase percentage in the experimental group A6-A10 after 40 piercing or insertion operations relative to the first piercing or insertion operation, represented by $((X_{40}-X_1)/X_1)*100\%$, is 6.1%, which lies in the experimental group A7; that is, in this embodiment, for all specimens of the experimental group A6-A10, the increase percentage of maximum piercing or insertion force of the 40th piercing or insertion operation relative to the first piercing or insertion operation, i.e., $((X_n-X_1)/X_1)*100\%$, is not greater than 6.1%. Under the same conditions, as shown in Table 3, for the comparative groups B6-B10 and C6-C10 in which the needle body of the 7/0 taper needle is not coated with the metallic glass material layer, when the number of piercing or insertion operations N is 40, the minimum increase percentage of maximum piercing or insertion force after 40 piercing or insertion operations relative to the first piercing or insertion operation is 42.9%, which lies in the comparative group B6. Accordingly, when the needle body is a curved 7/0 taper needle, the object is rubber, and the number of piercing or insertion operations N is 40, the greatest increase percentage of maximum piercing or insertion force after 40 piercing or insertion operations relative to the first piercing or insertion operation, represented by $((X_{40}-X_1)/X_1)*100\%$, of the experimental group A7 (6.1%), is not greater than 0.143-fold of the minimum increase percentage of maximum piercing or insertion force after 40 piercing or insertion operations relative to the first piercing or insertion operation of the comparative group B4 (42.9%).

In addition, 7/0 taper needles coated with the metallic glass material layer 20 in the experimental group A6-A10 show significantly inhibited increase percentage of maximum piercing or insertion force as compared with the comparative groups B6-B10 and C6-C10. According to the results in Table 3, for the specimens in the comparative group B6-B10 or the specimens in the comparative group C6-C10, both without the metallic glass material layer, after 40 piercing or insertion operations, the increase percentage of the maximum piercing or insertion force is at least 7-fold of the greatest increase percentage of the maximum piercing or insertion force of the specimens in the experimental group A6-A10 after 40 piercing or insertion operations, such as between 10-fold and 35-fold.

Also according to the results in Table 3, even using different types of structural design, the increase percentage of maximum piercing or insertion force of the medical needles in the experimental group A6-A10 after having performed 40 piercing or insertion operations relative to 1 piercing or insertion operation, is less than 10%, even less than 7%.

Figure 4:
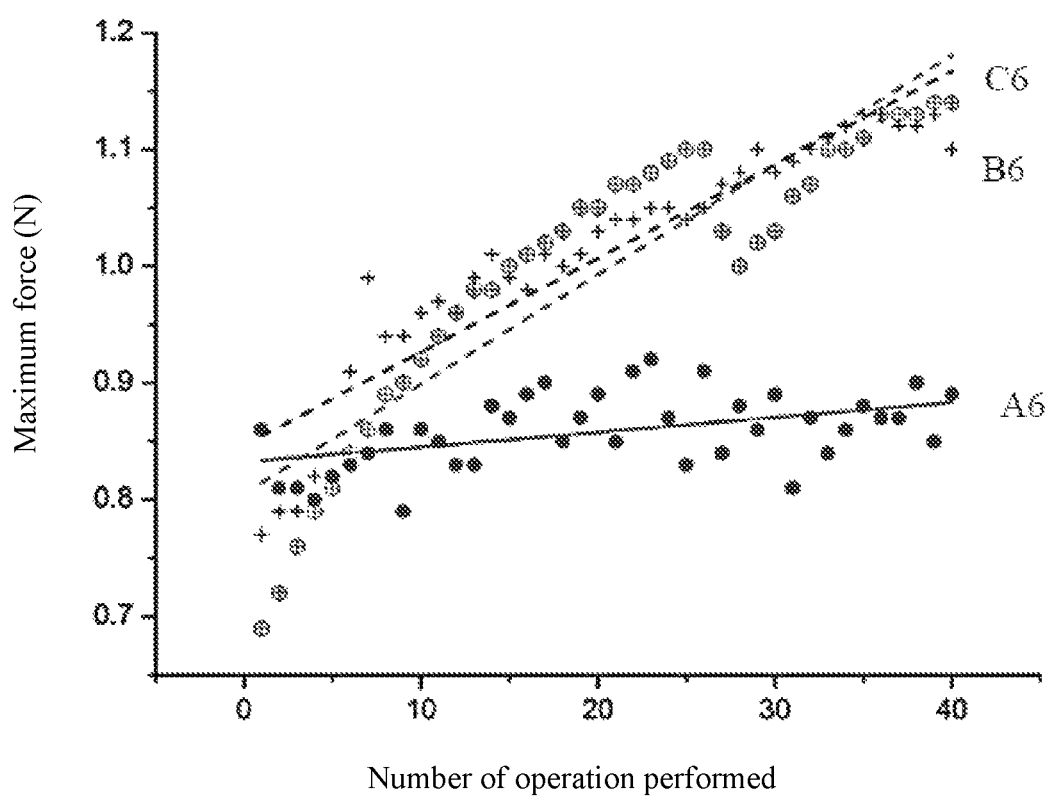
FIG. 4 illustrates a scatter plot of maximum piercing or insertion force of each of 40 piercing or insertion operations of the experimental group A6, comparative group B6 and comparative group C6 listed in Table 3.

Refer to FIG. 4. FIG. 4 illustrates a scatter plot of maximum piercing or insertion force of each of 40 piercing or insertion operations of the experimental group A6, comparative group B6 and comparative group C6 in Table 3, wherein the horizontal axis represents the number of piercing or insertion operation performed and the vertical axis represents the maximum piercing or insertion force corresponding to each operation. A simple linear regression may be made for each of the experimental group A6, comparative group B6 and comparative group C6 to obtain a trend line representing the ascending trend of maximum piercing or insertion force. As shown in FIG. 4, for the 7/0 taper needle coated with the metallic glass material layer 20 in the experimental group A6, the trend line has a gentle slope than those of the comparative groups B6 and C6, indicating that the medical needle of the present disclosure can effectively inhibit the increase of maximum piercing or insertion force caused by piercing operations, even if a different type of needle body is used. The slope of the trend line of the experimental group A6 is about 0.00127, significantly less than that of the comparative group B6 (0.00802) and that of the comparative group C6 (0.00938).

Furthermore, a simple linear regression may be made for each of the experimental group A6-A10, comparative group B6-B10 and comparative group C6-C10 to obtain a trend line and its slope representing the ascending trend of the maximum piercing or insertion force relative to the number of piercing or insertion operation. As shown in Table 3, the experimental group A6-A10, the comparative group B6-B10 and the comparative group C6-C10 all have a trend line with a positive slope; when the needle body is a curved 7/0 taper needle, the object is rubber, and the piercing or insertion operation number N is 40, a dataset of every n and $X_n$ of the piercing or insertion operations is characterized by having a slope of simple linear regression estimated using the ordinary least squares method, wherein the slope a' of each trend line of the experimental group A6-A10 is between 0.00023 and 0.00133, and the maximum slope 0.00133 lies in the experimental group A6; in other words, in this embodiment, the slope of the trend line of any one in the experimental group A6-A10 is not greater than 0.00654. As shown in Table 3, for the comparative group B6-B10 and the comparative group C6-C10 which represent 7/0 taper needles without the metallic glass material layer, under the same conditions, when the piercing or insertion operation number N is 40, a dataset of every n and $X_n$ of the piercing or insertion operations is also characterized by having a slope of simple linear regression estimated using the ordinary least squares method, wherein the slope a' of each trend line of the comparative group B6-B10 is between 0.00677 and 0.00909, and the slope a' of each trend line of the comparative group C6-C10 is between 0.00771 and 0.01028. According to the linear regression analysis above, the increase in maximum piercing or insertion force of the experimental group A6-A10 is significantly lower compared with the comparative groups B6-B10 and C6-C10, indicating that after multiple piercing or insertion operations, the metallic glass material layer 20 may serve as a solid lubricant layer of the medical needle to protect the needle body, thereby inhibiting the increase of piercing force required and enhancing the efficacy and durability.

In the following experiments, a commercial needle is unpacked, cleaned to remove the lubricant layer and then coated with the metallic glass material layer 20 to serve as the experimental group A11; on the other hand, a commercial needle unpacked and cleaned to remove the lubricant layer serves as the comparative group B11, and a commercial needle simply unpacked serve as the comparative group C11 in the piercing or insertion experiments. In this embodiment, 6/0 cutting needles and artificial blood vessels (such as those made of polymeric material, e.g., F8008C, CARBOFLO, or IMPRA® ePTFE® Vascular Grafts, 8 mm in diameter) are used. Each 6/0 cutting needle of the experimental group A11, comparative group B11 and comparative group C11, with the speed and depth of piercing or insertion operation set at 30 mm/min and 2.5 mm respectively, is subject to 40 piercing or insertion operations, and the maximum piercing or insertion force after every 10 piercing or insertion operations is recorded to calculate the percentage of increased maximum piercing or insertion force after every 10 piercing or insertion operations, as listed in Table 4.

TABLE 4

|     | 1 time | 10 times | increase percentage | 20 times | increase percentage | 30 times | increase percentage | 40 times | increase percentage |
|-----|--------|----------|---------------------|----------|---------------------|----------|---------------------|----------|---------------------|
| A11 | 0.36   | 0.36     | 0.0%                | 0.41     | 13.9%               | 0.4      | 11.1%               | 0.38     | 5.6%                |
| B11 | 0.47   | 0.51     | 8.5%                | 0.53     | 12.8%               | 0.51     | 8.5%                | 0.54     | 14.9%               |
| C11 | 0.47   | 0.54     | 14.9%               | 0.55     | 17.0%               | 0.54     | 14.9%               | 0.56     | 19.1%               |

According to the results in Table 4, wherein the rubber is replaced by artificial blood vessels as the object, for the specimen in the comparative group B11 or the specimen in the comparative group C11, both without the metallic glass material layer, after 40 piercing or insertion operations, the increase percentage of the maximum piercing or insertion force is at least 2-fold of the greatest increase percentage of the maximum piercing or insertion force of the specimens in the experimental group A11 after 40 piercing or insertion operations, such as between 2.5-fold and 4-fold.

Furthermore, according to the results in Table 4, even if a different type of object is used, the experimental group A11, after 40 piercing or insertion operations, shows an increase percentage of maximum piercing or insertion force, relative to 1 piercing or insertion operation, of less than 10%, such as between 0% and 10%.

Figure 5:
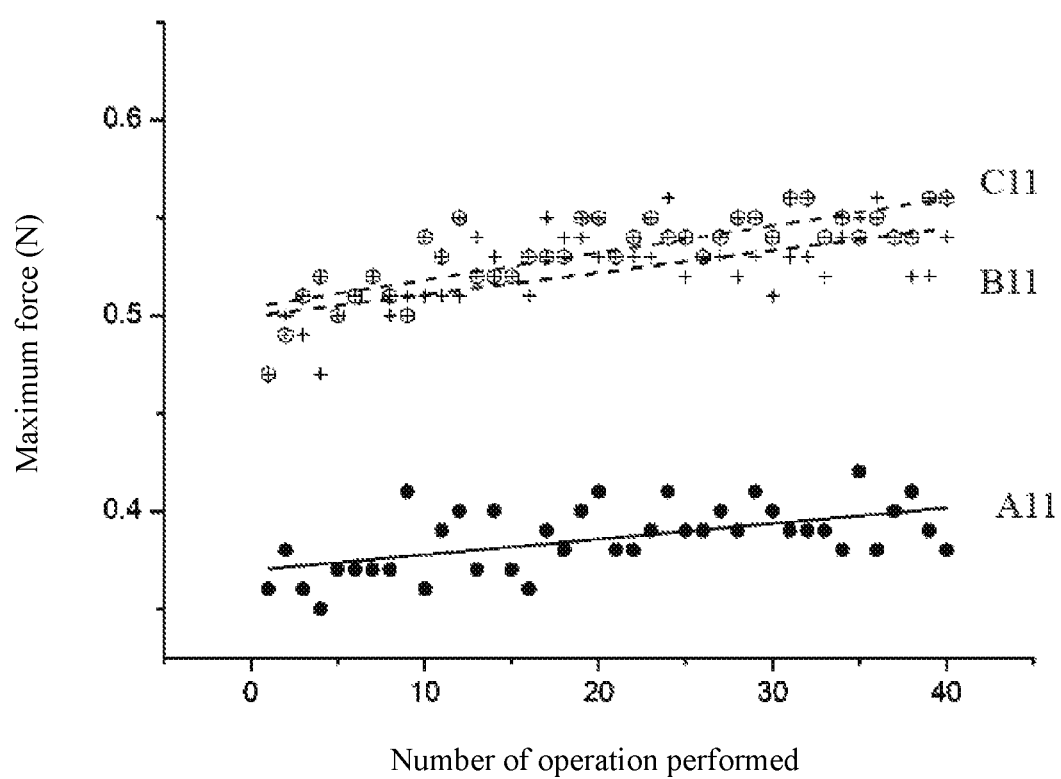
FIG. 5 illustrates a scatter plot of maximum piercing or insertion force of each of 40 piercing or insertion operations of the experimental group A11, comparative group B11 and comparative group C11 listed in Table 4.

Refer to FIG. 5. FIG. 5 illustrates a scatter plot of maximum piercing or insertion force of each of 40 piercing or insertion operations of the experimental group A11, comparative group B11 and comparative group C11 in Table 4, wherein the horizontal axis represents the number of piercing or insertion operation performed and the vertical axis represents the maximum piercing or insertion force corresponding to each operation. A simple linear regression may be made for each of the experimental group A11, comparative group B11 and comparative group C11 to obtain a trend line representing the ascending trend of maximum piercing or insertion force. As shown in FIG. 5, for the 6/0 cutting needle coated with the metallic glass material layer 20 in the experimental group A11, the trend line has a gentle slope than those of the comparative groups B11 and C11, indicating that the medical needle of the present disclosure can effectively inhibit the increase of maximum piercing or insertion force caused by piercing operations, even if a different type of object to be pierced or inserted is used.

Figure 6:
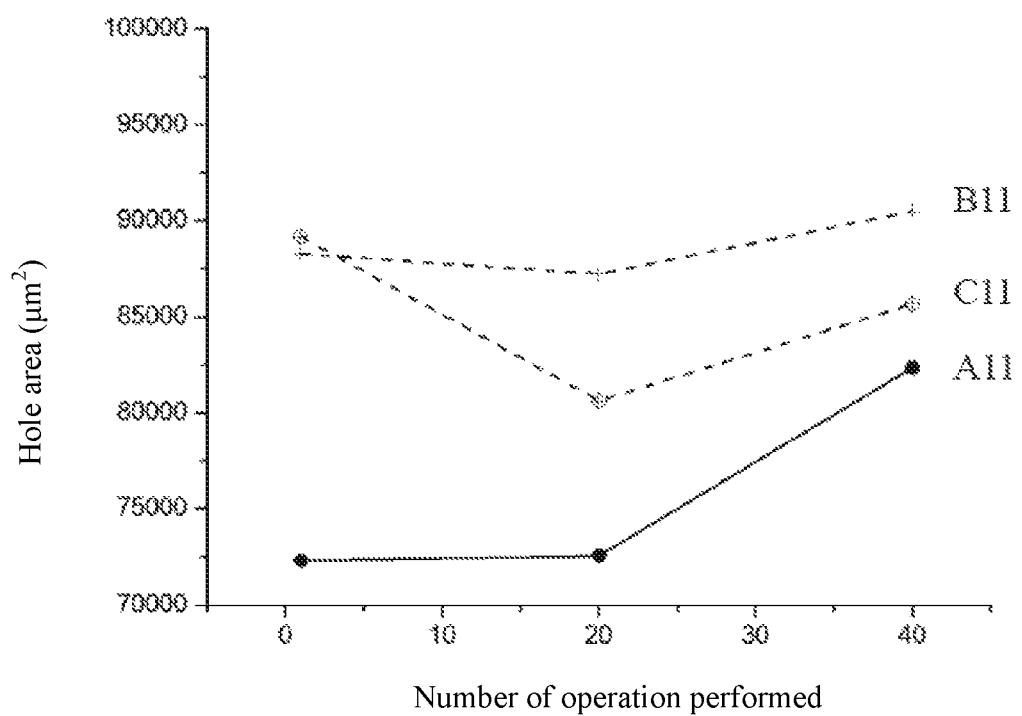
FIG. 6 illustrates the variation of hole area formed in the 1st, 20th and 40th piercing or insertion operation of the experimental group A11, comparative group B11 and comparative group C11 listed in Table 4.

Refer to FIG. 6. FIG. 6 illustrates the variation of hole area formed in the 1st, 20th and 40th piercing or insertion operation of the experimental group A11, comparative group B11 and comparative group C11 listed in Table 4, wherein the horizontal axis represents the number of piercing or insertion operation and the vertical axis represents the hole area (unit: $\mu m^2$) formed by the piercing or insertion operation. As shown in FIG. 6, for the 6/0 cutting needle coated with the metallic glass material layer 20 in the experimental group A11, the hole area formed in the 1st, 20th and 40th piercing or insertion operation is smaller than that of the comparative group B11 or C11, such as between 70000 $\mu m^2$ and 85000 $\mu m^2$. Accordingly, with the presence of the metallic glass material layer 20, the medical needle disclosed herein may effectively minimize the injury caused by piercing or insertion operations to the object, such as human tissues, and reduce bleeding during the suturing process.

In the following experiments, a commercial 18 G straight needle, with an outer diameter of about 1.27 mm, is unpacked, cleaned to remove the lubricant layer and then coated with the metallic glass material layer 20 to serve as the experimental group; on the other hand, another commercial 18 G straight needle unpacked and cleaned to remove the lubricant layer serves as the comparative group. A 8 cm×8 cm×3 cm cuboid rubber and a 9 cm×9 cm×3.5 cm multi-layer tissue from pig are used as the objects to be pierced or inserted, and each 18 G straight needle from the experimental group and comparative group is tested with the speed and depth of piercing or insertion operation set at 30 mm/min and 25 mm respectively to carry out single piercing or insertion operation. The objects having been subject to the piercing or insertion operation are then observed with an optical microscope to measure and record the area of hole thus formed. The results show that the needle of the experimental group forms a hole area of about 401,200 $\mu m^2$ on the cuboid rubber, and the needle of the comparative group forms a hole area of about 570,400 $\mu m^2$ on the cuboid rubber; in addition, the needle of the experimental group forms a hole area of about 81,000 $\mu m^2$ on the multi-layer tissue from pig, and the needle of the comparative group forms a hole area of about 153,800 $\mu m^2$ on the multi-layer tissue from pig. Therefore, for any object to be pierced or inserted, including cuboid rubber and multi-layer tissue from such as pig, the needle of the experimental group may achieve a reduced hole area, indicating that the medical needles according to the present disclosure, with the metallic glass material layer 20 coated thereon, may reduce the area of wound formed on such as human body tissues due to piercing or insertion operation, as compared with naked needles.

In the following experiments, commercial needles are unpacked, cleaned to remove the lubricant layer and then coated with the metallic glass material layer 20 to serve as the experimental group A12-A14; on the other hand, commercial needles unpacked and cleaned to remove the lubricant layer serve as the comparative group B12-B14, and needles simply unpacked serve as the comparative group C12-C14 in the piercing or insertion experiments. In this embodiment, curved 6/0 cutting needles and artificial blood vessels (such as those made of polymeric material, e.g., F8008C, CARBOFLO, or IMPRA® ePTFE® Vascular Grafts, 8 mm in diameter, having carbon lining on the inner wall to prevent thrombus) are used. Each 6/0 cutting needle of the experimental group A12-A14, comparative group B12-B14 and comparative group C12-C14, with the speed and depth of piercing or insertion operation set at 30 mm/min and 2.5 mm respectively, is subject to 40 piercing or insertion operations, and the maximum piercing or insertion force after every 10 piercing or insertion operations is recorded to calculate the percentage of increased maximum piercing or insertion force after every 10 piercing or insertion operations, as listed in Table 5.

In one embodiment, given that the needle body is a curved 6/0 cutting needle, the object is an artificial blood vessel made of polymeric material, and the piercing or insertion operation number N is 40, a dataset of every n and $X_n$ of the piercing or insertion operations is characterized by having a slope of simple linear regression estimated using the ordinary least squares method, wherein the slope a' of each trend line of the experimental group A12-A14 is between −0.00020 and −0.00047; in other words, in this embodiment, the slope of the trend line of any one in the experimental group A12-A14 is not greater than 0.00654, too. Accordingly, the slopes measured from the experimental group A12-A14 are all less than 0, such as between −0.00047 and −0.00020, all being negative values, indicating that the maximum piercing or insertion force decreases with the increase of piercing or insertion operations performed. As shown in Table 5, for the comparative group B12-B14 and the comparative group C12-C14 which represent 6/0 cutting needles without the metallic glass material layer, under the

TABLE 5

|     | 1 time | 10 times | increase percentage | 20 times | increase percentage | 30 times | increase percentage | 40 times | increase percentage | slope |
| --- | --- | --- | --- | --- | --- | --- | --- | --- | --- | --- |
| A12 | 0.65 | 0.66 | 1.5% | 0.68 | 4.6% | 0.67 | 3.1% | 0.64 | −1.5% | −0.00020 |
| A13 | 0.65 | 0.65 | 0.0% | 0.60 | −7.7% | 0.65 | 0.0% | 0.64 | −1.5% | −0.00047 |
| A14 | 0.60 | 0.63 | 5.0% | 0.64 | 6.7% | 0.61 | 1.7% | 0.63 | 5.0% | −0.00043 |
| B12 | 0.37 | 0.47 | 27.0% | 0.48 | 29.7% | 0.51 | 37.8% | 0.52 | 40.5% | 0.00299 |
| B13 | 0.37 | 0.45 | 21.6% | 0.49 | 32.4% | 0.48 | 29.7% | 0.52 | 40.5% | 0.00354 |
| B14 | 0.42 | 0.50 | 19.0% | 0.51 | 21.4% | 0.54 | 26.8% | 0.52 | 23.8% | 0.00194 |
| C12 | 0.45 | 0.53 | 17.8% | 0.50 | 11.1% | 0.54 | 20.0% | 0.56 | 24.4% | 0.00227 |
| C13 | 0.43 | 0.48 | 11.6% | 0.50 | 13.6% | 0.51 | 18.6% | 0.51 | 18.6% | 0.00170 |
| C14 | 0.45 | 0.51 | 13.3% | 0.53 | 17.8% | 0.56 | 24.4% | 0.54 | 20.0% | 0.00211 |

From the results in Table 5, with the presence of the metallic glass material layer 20 covering the surface of the 6/0 cutting needles, among all increase percentages of maximum piercing or insertion force after every 10 piercing or insertion operations relative to the first piercing or insertion operation in the experimental group A12-A14, experimental group A14 exhibits the greatest increase percentage of 6.7% after 20 piercing or insertion operations. That is, in this embodiment, for all specimens of the experimental group A12-A14, the increase percentage of maximum piercing or insertion force of a nth piercing or insertion operation relative to the first piercing or insertion operation, represented by $((X_n-X_1)/X_1)*100\%$, is not greater than 18.9%, too.

According to the results of the experimental group A12-A14 in Table 5, if the needle body is a curved 6/0 cutting needle, the object is an artificial blood vessel, and the number of piercing or insertion operation N is 40, the value of $((X_{40}-X_1)/X_1)*100\%$ of the experimental group A12-A14 is between −1.5% and 5%, indicating that the maximum piercing or insertion force after piercing or insertion operations may be reduced by 1.5%. In addition, as shown in Table 5, for the comparative group B12-B14 and the comparative group C12-C14 which represent 6/0 cutting needles without the metallic glass material layer, under the same conditions, when the piercing or insertion operation number N is 40, the increase percentage of maximum piercing or insertion force after 40 piercing or insertion operations relative to the first piercing or insertion operation in the comparative group B12-B14 is between 23.8% and 40.5%, and the increase percentage of maximum piercing or insertion force after 40 piercing or insertion operations relative to the first piercing or insertion operation in the comparative group C12-C14 is between 18.6% and 24.4%.

same conditions, when the piercing or insertion operation number N is 40, a dataset of every n and $X_n$ of the piercing or insertion operations is also characterized by having a slope of simple linear regression estimated using the ordinary least squares method, wherein the slope a' of each trend line of the comparative group B12-B14 is between 0.00194 and 0.00354, and the slope a' of each trend line of the comparative group C12-C14 is between 0.00170 and 0.00227.

Furthermore, according to the results in Table 5, even if a different type of object (i.e., artificial blood vessel) is used, the experimental group A12-A14, after 40 piercing or insertion operations, shows an increase percentage of maximum piercing or insertion force, relative to 1 piercing or insertion operation, of less than 10%, such as less than or equal to 5%.

In the following experiments, a commercial 18 G straight needle, with an outer diameter of about 1.27 mm, is unpacked, cleaned to remove the lubricant layer and then coated with the metallic glass material layer 20 to serve as the experimental group A15; on the other hand, a commercial 18 G straight needle unpacked and cleaned to remove the lubricant layer serves as the comparative group B15, and a commercial 18 G straight needle simply unpacked serves as the comparative group C15 in the piercing or insertion experiments. In this embodiment, rubber is used as the object to be pierced or inserted, and each 18 G straight needle of the experimental group A15, comparative group B15 and comparative group C15 is tested with the speed and depth of piercing or insertion operation set at 30 mm/min and 25 mm respectively to carry out 16 piercing or insertion operations; the maximum piercing or insertion force of every piercing or insertion operation is recorded for each 18 G straight needle to calculate the percentage of increased maximum piercing or insertion force after 16 piercing or insertion operations, as listed in Table 6.

TABLE 6

|     | 1 time | 2 times | 3 times | 4 times | 5 times | 6 times | 7 times | 8 times | 9 times | 10 times |
|-----|--------|---------|---------|---------|---------|---------|---------|---------|---------|----------|
| A15 | 8.31   | 8.38    | 8.51    | 8.53    | 8.57    | 8.53    | 8.52    | 8.47    | 8.52    | 8.46     |
| B15 | 9.25   | 9.36    | 9.38    | 9.52    | 9.58    | 9.62    | 9.53    | 9.57    | 9.61    | 9.65     |
| C15 | 9.23   | 9.66    | 9.76    | 9.8     | 9.72    | 9.78    | 9.76    | 9.89    | 9.92    | 9.98     |

|     | 1 time | 11 times | 12 times | 13 times | 14 times | 15 times | 16 times | increase percentage |
|-----|--------|----------|----------|----------|----------|----------|----------|---------------------|
| A15 | 8.31   | 8.44     | 8.38     | 8.29     | 8.27     | 8.25     | 8.16     | −1.81%              |
| B15 | 9.25   | 9.62     | 9.62     | 9.64     | 9.84     | 9.90     | 9.96     | 7.68%               |
| C15 | 9.23   | 10.00    | 10.06    | 9.99     | 10.03    | 10.03    | 10.03    | 8.67%               |

From the results in Table 6, after 16 piercing or insertion operations, the maximum piercing or insertion force of the comparative group B15 increases by about 7.68%, and the maximum piercing or insertion force of the comparative group C15 increases by about 8.67%; in contrast, the maximum piercing or insertion force of the experimental group A15 unexpectedly decreases; for example, the greatest increase percentage of maximum piercing or insertion force is 3.13%, after 5 piercing or insertion operations, and the lowest increase percentage of maximum piercing or insertion force is −1.81%, after 16 piercing or insertion operations; that is, in this embodiment, for the experimental group A15, the increase percentage of maximum piercing or insertion force of a nth piercing or insertion operation relative to the first piercing or insertion operation, represented by $((X_n-X_1)/X_1)*100\%$, is not greater than 18.9%, too. Therefore, even if a different needle (e.g., a 18 G straight needle) is used, with the increase of piercing or insertion operations, the medical needle of the present disclosure not only may still effectively inhibit the increase of maximum piercing or insertion force required, but also may reduce the maximum piercing or insertion force required.

Figure 7:
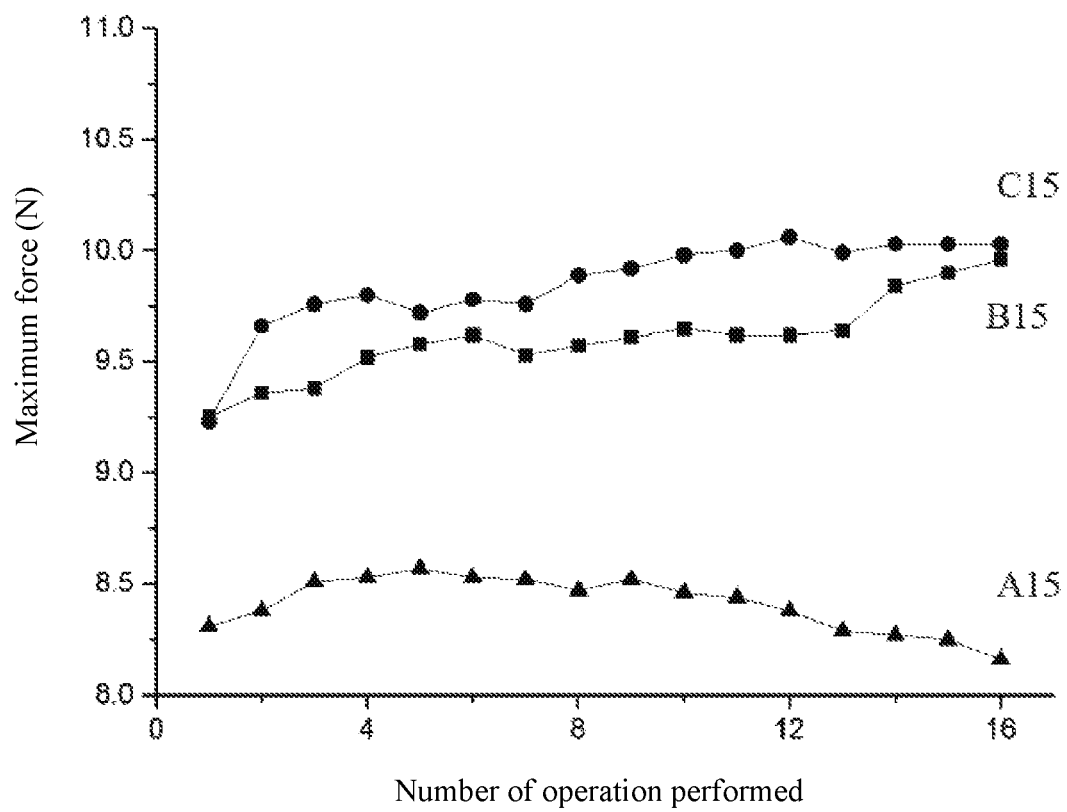
FIG. 7 illustrates a scatter plot of maximum piercing or insertion force of each of 16 piercing or insertion operations of the experimental group A15, comparative group B15 and comparative group C15 listed in Table 6.

Refer to FIG. 7. FIG. 7 illustrates a scatter plot of maximum piercing or insertion force of each of 16 piercing or insertion operations of the experimental group A15, comparative group B15 and comparative group C15, wherein the horizontal axis represents the number of piercing or insertion operation and the vertical axis represents the maximum piercing or insertion force corresponding to each operation. As shown in FIG. 7, for the 18 G straight needle coated with the metallic glass material layer 20 of experimental group A15, a descending trend can be observed, reflecting a slope of less than or equal to 0, completely different from the ascending trend observed from the comparative groups B15 and C15; in addition, the maximum piercing or insertion force of the experimental group A15 is significantly lower than that of the comparative groups B15 and C15.

In the following experiments, a commercial 21 G straight needle with an outer diameter of about 0.8192 mm and without any surface coating is coated with the metallic glass material layer 20 to serve as the experimental group A16; on the other hand, a commercial 21 G straight needle coated with a titanium nitride layer serves as the comparative group B16 in the piercing or insertion tests. In this embodiment, rubber is used as the object to be pierced or inserted, and each 21 G straight needle of the experimental group A16 and comparative group B16 is tested with the speed and depth of piercing or insertion operation set at 60 mm/min and 5 mm respectively to carry out 80 piercing or insertion operations; the maximum piercing or insertion force of every 10 piercing or insertion operations is recorded for each 21 G straight needle to calculate the percentage of increased maximum piercing or insertion force after every 10 piercing or insertion operations, as listed in Table 7.

TABLE 7

|     | 1 time | 10 times | increase percentage | 20 times | increase percentage | 30 times | increase percentage | 40 times | increase percentage |
|-----|--------|----------|---------------------|----------|---------------------|----------|---------------------|----------|---------------------|
| A16 | 4.26   | 4.49     | 5.4%                | 4.52     | 6.1%                | 4.58     | 7.5%                | 4.63     | 8.7%                |
| B16 | 5.09   | 5.48     | 7.7%                | 5.48     | 7.7%                | 5.56     | 9.2%                | 5.72     | 12.4%               |

|     | 1 time | 50 times | increase percentage | 60 times | increase percentage | 70 times | increase percentage | 80 times | increase percentage |
|-----|--------|----------|---------------------|----------|---------------------|----------|---------------------|----------|---------------------|
| A16 | 4.26   | 4.69     | 10.1%               | 4.71     | 10.6%               | 4.72     | 10.8%               | 4.78     | 12.2%               |
| B16 | 5.09   | 5.84     | 14.7%               | 5.80     | 13.9%               | 5.94     | 16.7%               | 6.20     | 21.8%               |

As shown in Table 7, the increase percentage of maximum piercing or insertion force after every 10 piercing or insertion operations of the experimental group A16, i.e., the 21 G straight needle coated with the metallic glass material layer 20, is less than that of the comparative group B16. In other words, according to the results in Table 7, the increase percentage of maximum piercing or insertion force of a medical needle, even using a 21 G straight needle, with the metallic glass material layer after having performed a certain number (e.g., no less than 10) of piercing or insertion operations is significantly less than that of a medical needle without the metallic glass material layer after having performed the same number of piercing or insertion operations.

Furthermore, according to the results in Table 7, even using a 21 G straight needle, the experimental group A16, after 40 piercing or insertion operations, shows an increase percentage of maximum piercing or insertion force, relative to 1 piercing or insertion operation, of less than 10%; similarly, even after 80 piercing or insertion operations, the experimental group A16 still shows an increase percentage of maximum piercing or insertion force relative to 1 piercing or insertion operation of less than 15%. Therefore, with the presence of the metallic glass material layer 20, the medical needle 1 of the present disclosure may maintain its sharpness after having performed multiple piercing or insertion operations and minimize injury to the object caused by piercing or insertion operation, thereby effectively inhibiting the increase percentage of the maximum piercing or insertion force after multiple piercing or insertion operations.

According to the present disclosure, given the medical needle 1 is a 6/0 cutting needle, a 7/0 straight needle, a 18 G straight needle, a 21 G straight needle or the like and the object to be pierced or inserted is rubber, artificial blood vessel or the like, relative to the first piercing or insertion operation, the medical needle 1 shows the following features: an increase percentage of the maximum piercing or insertion force of less than or equal to 15% after 10 piercing or insertion operations, such as between −15% and 15%, between −10% and 10% or between −5% and 5%, such as between 0% and 15% or between −15% and 0%; an increase percentage of the maximum piercing or insertion force of less than or equal to 20% after 20 piercing or insertion operations, such as between −15% and 20%, between −10% and 20%, between −5% and 15% or between 0% and 10%, preferably between −5% and 20%; an increase percentage of the maximum piercing or insertion force of less than or equal to 15% after 30 piercing or insertion operations, such as between −10% and 15%, between −5% and 10% or between 0% and 5%, preferably between −5% and 15%; an increase percentage of the maximum piercing or insertion force of less than or equal to 15% after 40 piercing or insertion operations, such as between −10% and 15%, between −5% and 10% or between 0% and 5%, preferably between −5% and 15%. In addition, under the same conditions, when using any one of the aforesaid or other needles and any one of the aforesaid or other objects to be pierced or inserted, the medical needle 1 disclosed herein, when the piercing or insertion operation number N is not greater than 10, the increase percentage of maximum piercing or insertion force of the nth piercing or insertion operation relative to the first piercing or insertion operation is less than or equal to 15%, such as between −15% and 15%, between −10% and 10% or between −5% and 5%, such as between 0% and 15% or between −15% and 0%; when the piercing or insertion operation number N is not greater than 40, the increase percentage of maximum piercing or insertion force is less than or equal to 20%, such as between −10% and 20%, such as between −5% and 15%.

Accordingly, the medical needle 1 disclosed herein, compared with needles with a lubricant layer or without any layer, by having the metallic glass material layer 20 coated on the needle body 10 as a protective coating, may maintain its sharpness and inhibit the increase of maximum piercing or insertion force percentage after having performed multiple piercing or insertion operations, thereby providing durability, effectively shortening the surgery time costs and preventing waste of resources.

Figure 8:
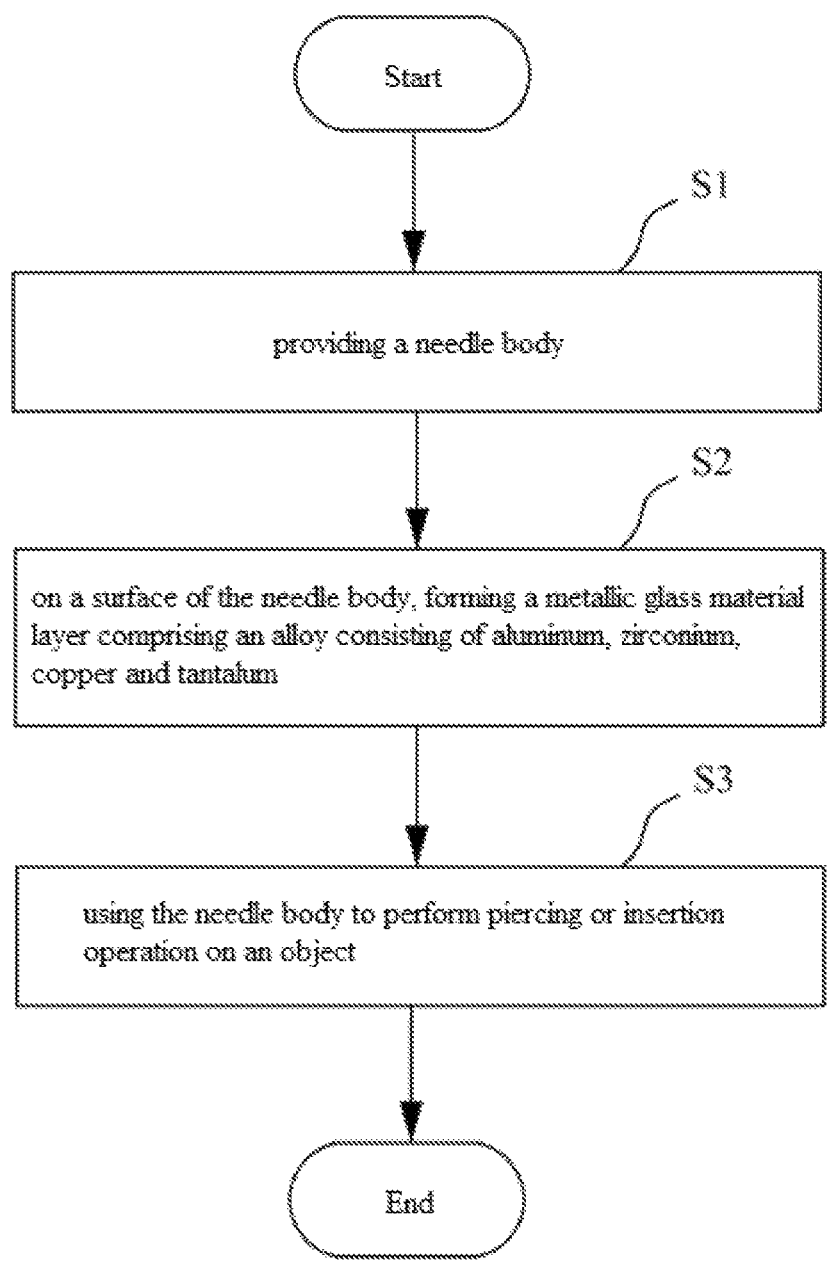
FIG. 8 illustrates a flow chart of a method of maintaining sharpness of a needle in one embodiment.

Refer to FIG. 8. FIG. 8 illustrates a flow chart of a method of maintaining sharpness of a needle in one embodiment. The method of maintaining sharpness of a needle comprises: providing a needle body 10 (Step S1); on a surface of the needle body 10, forming a metallic glass material layer 20 (Step S2), wherein the metallic glass material layer 20 comprises an alloy consisting of aluminum, zirconium, copper and tantalum, such that the metallic glass material layer 20 serves as the covering and protecting layer of the needle body 10; and using the needle body 10 to perform N times of piercing or insertion operation on an object, wherein the depth of each piercing or insertion operation ranges from 1 to 10 mm, the speed of each piercing or insertion operation ranges from 10 to 100 mm/min, and N ranges from 5 to 80 inclusive (Step S3). With the presence of the metallic glass material layer 20 covering the needle body 10, an increase percentage of maximum piercing or insertion force of a nth piercing or insertion operation relative to the first piercing or insertion operation using the needle body 10 is not greater than 18.9% given that n is a natural number from 5 to N.

The above detailed description is merely illustrative in nature and is not intended to limit the embodiments of the subject matter or the application and uses of such embodiments. Moreover, while at least one exemplary example or comparative example has been presented in the foregoing detailed description, it should be appreciated that a vast number of variations exist. It should also be appreciated that the exemplary one or more embodiments described herein are not intended to limit the scope, applicability, or configuration of the claimed subject matter in any way. Rather, the foregoing detailed description will provide those skilled in the art with a convenient guide for implementing the described one or more embodiments. Also, various changes can be made in the function and arrangement of elements without departing from the scope defined by the claims, which include known equivalents and foreseeable equivalents at the time of filing this patent application.

What is claimed is:

1. A medical needle used for performing a piercing or insertion operation on an object repetitively, the medical needle comprising:
    a needle body; and
    a metallic glass material layer formed on a surface of the needle body, the metallic glass material layer comprising an alloy consisting of aluminum, zirconium, copper and tantalum;
    wherein the presence of the metallic glass material layer covering the needle body maintains a sharpness of the medical needle such that an increase percentage of a maximum piercing or insertion force of a nth piercing or insertion operation relative to a first piercing or insertion operation, represented by $((X_n-X_1)/X_1)*100\%$, is not greater than 18.9%, given that: N represents the number of piercing or insertion operations performed by the medical needle on the object and ranges from 5 to 80 inclusive; n is a natural number from 5 to N; $X_1$ represents the maximum piercing or insertion force required for the first piercing or insertion operation; and $X_n$ represents the maximum piercing or insertion force required for the nth piercing or insertion operation;
    wherein the metallic glass material layer is formed by a magnetron sputtering process in which the needle body and a target are placed in a vacuum environment with a work pressure of 0.5 to 4 mTorr, a distance between the needle body and the target is set at 8 to 12 cm, a radio frequency energy is provided between the needle body and the target, and the power density of the target is 3.65 to 10.96 W/cm$^2$; and the metallic glass material layer thus formed has a surface roughness of between 0.44 and 0.54 nm.

2. The medical needle of claim 1, wherein the needle body is a curved 6/0 cutting needle and the object is a rubber, and wherein when N is 40, the value of $((X_{40}-X_1)/X_1)*100\%$ of the medical needle is not greater than 0.337-fold of that of a needle body without the metallic glass material layer.

3. The medical needle of claim 1, wherein the needle body is a curved 7/0 taper needle and the object is a rubber, and wherein when N is 40, the value of $((X_{40}-X_1)/X_1)*100\%$ of the medical needle is not greater than 0.143-fold of that of a needle body without the metallic glass material layer.

4. The medical needle of claim 1, wherein the needle body is a curved 6/0 cutting needle and the object is a rubber, and wherein when N is 40, the value of $((X_{40}-X_1)/X_1)*100\%$ is not greater than 9.9%.

5. The medical needle of claim 1, wherein the needle body is a curved 7/0 taper needle and the object is a rubber, and wherein when N is 40, the value of $((X_{40}-X_1)/X_1)*100\%$ is not greater than 6.1%.

6. The medical needle of claim 1, wherein the needle body is a curved 6/0 cutting needle and the object is an artificial blood vessel made of polymeric material, and wherein when N is 40, the value of $((X_{40}-X_1)/X_1)*100\%$ is between −1.5% and 5%.

7. The medical needle of claim 1, wherein the needle body is selected from a cutting needle, a taper needle, a straight needle and a curved needle.

8. The medical needle of claim 1, wherein the metallic glass material layer has an amorphous structure which renders a broad diffraction peak only between 30° and 40° as measured by X-ray diffraction.

9. The medical needle of claim 1, wherein the metallic glass material layer comprises $Zr_{53}Cu_{33}Al_9Ta_5$.

10. The medical needle of claim 1, wherein the metallic glass material layer has a hardness of 700 to 2000 HV.

11. A medical needle used for performing a piercing or insertion operation on an object repetitively, the medical needle comprising:
a needle body; and
a metallic glass material layer formed on a surface of the needle body, the metallic glass material layer comprising an alloy consisting of aluminum, zirconium, copper and tantalum;
wherein, given that the medical needle is subject to N times of piercing or insertion operation, wherein N ranges from 5 to 80 inclusive, and given that a maximum piercing or insertion force of a nth piercing or insertion operation is $X_n$, wherein n is a natural number from 1 to N, a dataset of every n and $X_n$ in the N times of piercing or insertion operation is characterized by having a slope of simple linear regression estimated using the ordinary least squares method of not greater than 0.00654 as calculated according to the formula below:

$$a' = \sum_{n=1}^{N} (X_n - \overline{X_N})(n - \overline{N}) / \sum_{n=1}^{N} (X_n - \overline{X_N})^2$$

wherein a' represents the slope, $\overline{X_N}$ represents an average maximum piercing or insertion force during the N times of piercing or insertion operation, and $\overline{N}$ represents an average of 1 to N,
wherein the metallic glass material layer is formed by a magnetron sputtering process in which the needle body and a target are placed in a vacuum environment with a work pressure of 0.5 to 4 mTorr, a distance between the needle body and the target is set at 8 to 12 cm, a radio frequency energy is provided between the needle body and the target, and the power density of the target is 3.65 to 10.96 W/cm²; and the metallic glass material layer thus formed has a surface roughness of between 0.44 and 0.54 nm.

12. The medical needle of claim 11, wherein the slope is a negative value.

13. The medical needle of claim 11, wherein the needle body is a curved 6/0 cutting needle and the object is a rubber, and wherein when N is 40, the slope is between 0.00131 and 0.00654.

14. The medical needle of claim 11, wherein the needle body is a curved 7/0 taper needle and the object is a rubber, and wherein when N is 40, the slope is between 0.00023 and 0.00133.

15. The medical needle of claim 11, wherein the needle body is a curved 6/0 cutting needle and the object is an artificial blood vessel made of polymeric material, and wherein when N is 40, the slope is between −0.00020 and −0.00047.

16. A method of maintaining sharpness of a needle, comprising:
providing a needle body;
on a surface of the needle body, forming a metallic glass material layer comprising an alloy consisting of aluminum, zirconium, copper and tantalum, wherein the metallic glass material layer is formed by a magnetron sputtering process in which the needle body and a target are placed in a vacuum environment with a work pressure of 0.5 to 4 mTorr, a distance between the needle body and the target is set at 8 to 12 cm, a radio frequency energy is provided between the needle body and the target, and the power density of the target is 3.65 to 10.96 W/cm², and the metallic glass material layer thus formed has a surface roughness of between 0.44 and 0.54 nm; and
using the needle body to perform N times of piercing or insertion operation on an object, wherein the depth of each piercing or insertion operation ranges from 1 to 10 mm, the speed of each piercing or insertion operation ranges from 10 to 100 mm/min, and N ranges from 5 to 80 inclusive;
wherein an increase percentage of a maximum piercing or insertion force of a nth piercing or insertion operation relative to a first piercing or insertion operation is not greater than 18.9% given that n is a natural number from 5 to N.

\* \* \* \* \*